United States Patent [19]

Kuzuya et al.

[11] Patent Number: 4,713,376

[45] Date of Patent: Dec. 15, 1987

[54] DEMENTIA-IMPROVING AND THERAPEUTIC AGENTS

[75] Inventors: Fumio Kuzuya, Nagoya; Hidetoshi Endo, Ichinomiya, both of Japan

[73] Assignee: Toyama Chemical Co., Ltd., Tokyo, Japan

[21] Appl. No.: 930,452

[22] Filed: Nov. 14, 1986

[30] Foreign Application Priority Data

Nov. 19, 1985 [JP] Japan .................. 60-257881

[51] Int. Cl.$^4$ .......................... A61K 31/685
[52] U.S. Cl. .................................... 514/78
[58] Field of Search ........................ 514/78

[56] References Cited

U.S. PATENT DOCUMENTS 3,803,214 4/1974 Miura et al. .............. 260/484 A
3,903,137 9/1975 Miura et al. .............. 260/484 A

FOREIGN PATENT DOCUMENTS 21490 6/1977 Japan .
37334 10/1978 Japan .
1251 1/1980 Japan .
2121405 4/1985 United Kingdom .

Primary Examiner—Stanley J. Friedman
Attorney, Agent, or Firm—Oblon, Fisher, Spivak, McClelland, & Maier

[57] ABSTRACT

An improving and therapeutic agent for neuropsychiatric symptoms accompanying dementia, which comprises, as an active ingredient, an acyloxyalkanoylcholine salt represented by the following general formula:

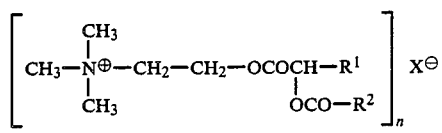

wherein $R^1$ and $R^2$, which may be the same or different, represent lower alkyl groups of 1 to 5 carbon atoms; X represents a sulfonic acid residue; and n is the same as the number of the sulfonyloxy groups of the sulfonic acid residue and represents an integer of 1 to 4.

5 Claims, No Drawings

DEMENTIA-IMPROVING AND THERAPEUTIC AGENTS

This invention relates to a new application of aclatonium napadisilate widely used as a drug, particularly as an excitomotor for digestive tract. More particularly, this invention relates to an improving and therapentic agent for neuropsychiatric symptoms accompanying senile dementia of Alzheimer's type, Alzheimer's disease and multi-infarct dementia (another name: cerebrovascular dementia), all of which are increasingly attracting attention in recent years.

Dementia is a serious disease because it reduces the cognitive function of patients and consequently deteriorates their social and/or occupational ability drastically. It is defined as a state of people accompanied with dysmnesia, disturbance of abstract thinking, disturbance of judgement, other serious disorders of intellectual ability and change of characters. Dementia is largely classified into senile dementia of Alzheimer's disease and multi-infarct dementia.

In demented patients, the amount of neurotransmitters in brain, particularly an acetylcholine is drastically reduced in each site of brain.

Also in demented patients, enlargement of cerebral ventricle and cerebral atrophy are seen at the brain CT. Because of these phenomena, the patient clearly has, in particular, reduced spontaneousness; abnormal action; neuropsychiatric symptoms in cognitive and mental function, speech, emotion and the like; subjective symptom; neurosis and ataxia in daily life. Since these disorders proceed irreversibly, the patient becomes invalid finally.

As drugs of dementia, currently there have mainly been used cerebral-metabolic improvement agents and cerebral vasodilators.

The cause of dementia has not yet been clarified. However, since cholinergic deficits in brain is confirmed in senile dementia of Alzheimer's type and Alzheimer's disease, various substances for activating the cholinergic system have been tested, but none of them have satisfactory effects.

As a result of research on various compounds, the present inventors have found that acyloxyalkanoylcholine salts represented by the general formula [I]:

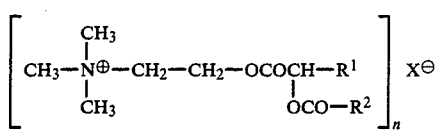

wherein $R^1$ and $R^2$, which may be the same or different, represent lower alkyl groups of 1 to 5 carbon atoms; X represents a sulfonic acid residue; and n is the same as the number of the sulfonyloxy groups of the sulfonic acid residue and represents an integer of 1 to 4, are effective for the improvement of neuropsychiatric symptoms accompanying senile dementia of Alzheimer's type, Alzheimer's disease and multi-infarct dementia.

An object of this invention is to provide an improving and therapeutic agent for neuropsychiatric symptoms accompanying dementia, which comprises, as an active ingredient, a compound represented by the general formula [I] (hereinafter also referred to as the present compound).

The present compounds are known, and Japanese Patent Publication Nos. 21,490/77, 37,334/78 and 1,251/80 describe that these compounds act as an excitomotor for digestive tract. However, the present compounds have not been known at all as an improving and therapeutic agent for neuropsychiatric symptoms accompanying dementia.

The present compounds [I] can be produced according to the processes described in the above patent publications.

This invention will be further explained in detail below.

In the general formula [I], $R^1$ and $R^2$ represent lower alkyl groups of 1 to 5 carbon atoms. The lower alkyl group includes, for example, methyl, ethyl, propyl, butyl and pentyl. The sulfonic acid having the sulfonic acid residue represented by X implies a monosulfonic acid, a disulfonic acid, a trisulfonic acid or a tetrasulfonic acid. The monosulfonic acid includes, for example, alkanesulfonic acids such as methanesulfonic acid, ethanesulfonic acid and the like; arenesulfonic acids such as benzenesulfonic acid, toluene-2-sulfonic acid, toluene-4-sulfonic acid, naphthalene-1-sulfonic acid, naphthalene-2-sulfonic acid and the like; aralkanesulfonic acids such as phenylmethanesulfonic acid and the like; cyclohexylsulfamic acid; camphor-3-sulfonic acid; camphor-8-sulfonic acid; camphor-10-sulfonic acid; and so forth. The disulfonic acid includes, for example, arenedisulfonic acids such as benzene-1,3disulfonic acid, toluene-3,5-disulfonic acid, naphthalene-1,5-disulfonic acid, naphthalene-2,6-disulfonic acid, naphthalene-2,7-disulfonic acid and the like. The trisulfonic acid includes, for example, arenetrisulfonic acids such as benzene-1,3,5-trisulfonic acid, benzene-1,2,4-trisulfonic acid, naphthalene-1,3,5-trisulfonic acid and the like. The tetrasulfonic acid includes, for example, arenetetrasulfonic acids such as naphthalene-1,3,5,7-tetrasulfonic acid and the like. The alkyl or aryl groups of these sulfonic acids may have a substituent or substituents.

One preferable example of the present compound is a compound of the general formula [I] in which each of $R^1$ and $R^2$ is a methyl group, X is a 1,5-naphthalenedisulfonic acid residue and n is 2, namely, a compound having the following structural formula:

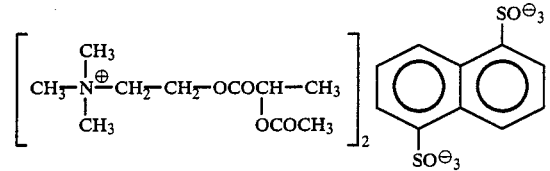

(hereinafter, this compound is referred to as aclatonium napadisilate).

The following clinical cases clarify that the present compound has a cerebral metabolic improvement activity which is suitable for use as a dementia-improving and therapeutic agent.

The degree of dementia was diagnosed in patients on the basis of DSM-III criteria with reference to the neuropsychiatric symptoms and findings of the CT scan of the head regions.

The overall improvement degree of the present drug was evaluated from the neuropsychiatric symptoms, scores of activity of daily living and Hasegawa's rating scales.

Clinical Case 1

Case T. I., a 77-year-old female, senile dementia of Alzheimer's type (Overall severity: Marked high degree)

She began to have a forgetfulness from approx. 4 years ago, and became spiritless and became unable to work, and became not to express her feeling, and had wanderling impulsion. The cerebral atrophy was generally noted by the finding of CT scan of head regions at the admission. Even though the treatment was conducted with various drugs, its efficacy was ineffective, and she lived almost on her bed, but when 300 mg/day of the present drug was administered, she could gait to outside of room at the 2nd week, and her movement behavior was improved, and spontaneousness increased and feeling became clear.

The overall improvement degree was judged as improvement.

Clinical Case 2

Case H. N., a 82-year-old male, senile dementia of Alzheimer's type (Overall severity: Marked high degree)

He had occasionally a forgetfulness from approx. 10 years ago, and became unable to do agricultural work from approx. 4 years ago. The diffuse cerebral atrophy was noted by the finding of CT scan of head regions at the admission. The decrease of conversation frequency, decrease of spontaneousness, malaise, etc. were noted, but when the present drug was administered, spontaneousness increased, and conversation with other patients increased, and he had favorable communication and became fortunate.

The overall improvement degree was judged as slight improvement.

Clinical Case 3

Case H. A., a 75-year-old female, senile dementia of Alzheimer's type (Overall severity: Moderate degree)

She began to have a forgetfulness from approx. 2 years ago, and became unable to do household affairs from 1 year ago, and became unable to distinguish her familial faces. The cerebral atrophy and enlargement of cerebral ventricle were noted by the finding of CT scan of head regions at the admission. The treatment was changed to the administration of 300 mg/day of the present drug because the efficacy was ineffective with other cerebral metabolic improvement drugs and cerebral-vasodilators. No changes were noted in the intellectual function, but decrease of spontaneousness and disturbance of emotion were improved. Namely, before the administration of the present drug, she lived almost on bed, and decrease of concern of the circumferences, decrease of will to daily life movement and scanty expression were noted, while from approx. 2nd week after administration, she became able to sit and gait, and eat food by herself and expression became clear.

The overall improvement degree was judged as slight improvement.

Clinical Case 4

Case S. H., a 92-year-old female, senile dementia of Alzheimer's type (overall severity: Moderate degree)

She began to have a forgetfulness and spiritlessness after operation of fracture of neck of femur from 10 years ago. The disorientation was strongly noted from 2-3 years ago. The cerebral atrophy and enlargement of cerebral ventricle were noted by the finding of CT scan of head regions at the admission. The efficacy was ineffective with other various drugs than the present drug. Slight decrease of spontaneousness and decrease of conversation frequency were noted, and she did not go out from her room. Therefore, the treatment was changed to the administration of 300 mg/day of the present drug, and from the 2nd week after the administration, her conversation frequency with other patients increased and she became able to go out from her room and occasionally go to toilet.

The overall improvement degree was judged as slight improvement.

Clinical Case 5

Case H. O. a 58-year-old male, Alzheimer's disease (Overall severity: Moderate degree)

He became occasionally aware of slight change of character from 8 years ago, and he lived without specific changes, but he became spiritless and not to express his feeling from 3 years ago. At the admission, he could not work entirely and was spiritless, and had contact disturbance with other patients, and decrease of memory power and judgement power were noted. He had a diabetes mellitus as a complication, but it was comparatively slight and he was subjected to diet therapy. The atrophy of anterior lobe was remarkably noted at the finding of CT scan of head regions at the admission. The increase of movement frequency and improvement of decrease of spontaneousness were noted at the 4th week of the administration of the present drug, and protection with family became easy. Moreover, defecation became smooth, and improvement was noted.

The overall improvement degree was judged as improvement.

In all of the above clinical cases, the present drug could be administered safely with no side effect.

As appreciated from the foregoing, administration of aclatonium napadisilate is effective for the improvement of neuropsychiatric symptoms accompanying dementia, although its effect on cognitive function has not been confirmed at this time, and the present drug is very advantageous as a drug exceeding the present drug-therapeutic limit and makes the management of demented patients easy.

The transference of aclatonium napadisilate into brain was found, whereby the cerebral metabolism was stimulated and the clinical effect of the compound was confirmed. Moreover, the effect of the compound even on severe dementia was also confirmed. These facts are believed to be very significant.

Next, among the present compounds [I], α-acetoxy-α-methylacetic acid trimethylammonioethyl ester toluene-4-sulfonate (hereinafter referred to as ALT) and bis(α-acetoxy-α-methylacetic acid trimethylammonioethyl ester) naphthalene-1,5-disulfonate (general name: aclatonium napadisilate) were heated for mouse acute toxicity by intraperitoneal injection as well as for hygroscopicity and stability. The results are shown in Table 1 and Table 2.

TABLE 1

| | Mouse acute toxicity $LD_{50}$ (mg/kg) |
|---|---|
| ALT | 657 |

TABLE 1-continued

| | Mouse acute toxicity LD$_{50}$ (mg/kg) |
|---|---|
| Aclatonium napadisilate | 636 |

TABLE 2

| Stored for 10 days at room temperature (30° C.) at a relative humidity of 55%. | | |
|---|---|---|
| | Appearance | Hygroscopicity *1 (%) | Decomposition percentage *2 (%) |
| ALT | No change | 0.6 | 0.5 |
| Aclatonium napadisilate | No change | 0.1 | 0.2 |

*1 Hygroscopicity (%) = (Increased weight)/(Original weight) × 100
*2 Measured in accordance with the hydroxylamine method for ester (Jikken Kagaku Koza, Vol. 24 Seibutsu Kagaku II, p 253 to 255, Maruzen). Decomposition percentage (%) = [1 − (absorbance of test sample)/(absorbance of standard solution)] × 100

As is obvious from the above clinical tests, Table 1 and Table 2, the present compound [I] transfers into brain, stimulates cerebral metabolism, has a clinically effective pharmaceutical activity and is very low in hygroscopicity and high in stability. When the present compound is used as an improving and therapeutic agent for neuropsychiatric symptoms accompanying dementia, they are formed into a tablet, a capsule, a powder, a syrup, a granule or the like, in accordance with a conventional method using an appropriate carrier generally used in drug preparation. The route, amount and number of administrations of the present compound can be varied appropriately depending upon the symptom of patient. Ordinarily, it is sufficient that the present compound is administered to adults in an amount of 150 to 450 mg/day, preferably 300 mg/day, in one to several portions.

The present compound can be formed into, for example, a powder by mixing it with an excipient such as starch, cellulose or the like and/or other adjuvants according to a conventional method. Other drug forms can also be prepared according to a general method.

Preparation examples are as follows:

PREPARATION EXAMPLE 1

A capsule containing 50 mg/capsule of aclatonium napadisilate, having the following formulation, can be produced in a known manner:

| Aclatonium napadisilate | 50 mg |
|---|---|
| Corn starch | 225 mg |
| Excipient | 25 mg |
| | 300 mg/capsule |

PREPARATION EXAMPLE 2

A granule containing 100 mg/granule of aclatonium napadisilate, having the following formulation, can be produced in a known manner;

| Aclatonium napadisilate | 100 mg |
|---|---|
| Corn starch | 850 mg |
| Excipient | 50 mg |
| | 1,000 mg/granule |

PREPARATION EXAMPLE 3

A table containing 50 mg/tablet of aclatonium napadisilate, having the following formulation, can be produced in a known manner;

| Aclatonium napadisilate | 50 mg |
|---|---|
| Corn starch | 300 mg |
| Excipient | 25 mg |
| | 375 mg/tablet |

What is claimed is:

1. A method of treating neuropsychiatric symptoms accompanying dementia in said patient which comprises administering to a patient a therapeutically effective amount of a therapeutic agent comprising, as an active ingredient, an acyloxyalkanoylcholine salt represented by the following formula:

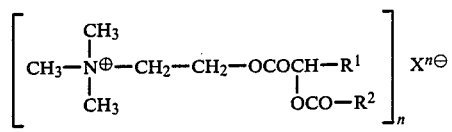

wherein R$^1$ and R$^2$, which may be the same or different, represent lower alkyl groups of 1 to 5 carbon atoms; X represents a sulfonic acid residue; and n is the same as the number of the sulfonyloxy groups of the sulfonic acid residue and represents an integer of 1 to 4.

2. A method according to claim 1, wherein the dementia is senile dementia of Alzheimer's type.

3. A method according to claim 1, wherein the dementia is Alzheimer's disease.

4. A method according to claim 1, wherein the dementiak is multi-infarct dementia.

5. A method according to claim 1, wherein the acyloxyalkanoylcholine salt is bis (α-acetoxy-α-methylacetic acid trimethylammonioethyl ester) naphthalene-1,5-disulfonate.

* * * * *